United States Patent
Cappy et al.

(10) Patent No.: US 11,478,634 B2
(45) Date of Patent: Oct. 25, 2022

(54) OPTICAL SENSOR

(71) Applicants: ÉCOLE CENTRALE DE LILLE, Villeneuve d'Ascq (FR); UNIVERSITÉ POLYTECHNIQUE HAUTS-DE-FRANCE, Valenciennes (FR); CENTRE NATIONAL DE LA RECHERCHE SCIENTIFIQUE, Paris (FR); YNCREA HAUTS DE FRANCE, Lille (FR); UNIVERSITE DE LILLE, Lille (FR)

(72) Inventors: Alain Cappy, Genech (FR); Francois Danneville, Lille (FR); Virginie Hoel, Lomme (FR); Christophe Loyez, Festubert (FR); Ilias Sourikopoulos, Mons en Baroeul (FR)

(73) Assignees: ÉCOLE CENTRALE DE LILLE, Villeneuve d'Ascq (FR); UNIVERSITÉ POLYTECHNIQUE HAUTS-DE-FRANCE, Valenciennes (FR); CENTRE NATIONAL DE LA RECHERCHE SCIENTIFIQUE, Paris (FR); YNCREA HAUTS DE FRANCE, Lille (FR); UNIVERSITE DE LILLE, Lille (FR)

( * ) Notice: Subject to any disclaimer, the term of this patent is extended or adjusted under 35 U.S.C. 154(b) by 0 days.

(21) Appl. No.: 16/758,583

(22) PCT Filed: Oct. 24, 2018

(86) PCT No.: PCT/EP2018/079119
§ 371 (c)(1),
(2) Date: Apr. 23, 2020

(87) PCT Pub. No.: WO2019/081562
PCT Pub. Date: May 2, 2019

(65) Prior Publication Data
US 2020/0346004 A1    Nov. 5, 2020

(30) Foreign Application Priority Data

Oct. 25, 2017   (FR) .................................... 1760062

(51) Int. Cl.
*A61N 1/05*    (2006.01)
*A61N 1/36*    (2006.01)
(Continued)

(52) U.S. Cl.
CPC ....... *A61N 1/0543* (2013.01); *A61N 1/36046* (2013.01); *A61N 1/36125* (2013.01);
(Continued)

(58) Field of Classification Search
CPC .............. A61N 1/0543; A61N 1/36046; A61N 1/36125; A61N 1/36128; G01J 1/46;
(Continued)

(56) References Cited

U.S. PATENT DOCUMENTS 5,024,223 A    6/1991    Chow
5,865,839 A    2/1999    Doorish
(Continued)

FOREIGN PATENT DOCUMENTS

DE    19921399 A1    11/2000
FR    2953394 A1    6/2011
FR    3050050 A1    10/2017

OTHER PUBLICATIONS

Yang Ni, Yi Ming Zhu, Bogdan Arion, "A 768×576 Logarithmic Image Sensor with Photodiode in Solar Cell mode," Jun. 9, 2011, International Image Sensor Workshop (IISW), lecture R35 (Year: 2011).*

(Continued)

*Primary Examiner* — Thanh Luu
*Assistant Examiner* — Monica T Taba
(74) *Attorney, Agent, or Firm* — Shumaker, Loop & Kendrick, LLP

(57) ABSTRACT

An optical sensor, especially an artificial retina, that includes at least one photosensitive cell. Each cell includes a integration capacitor, a read circuit the operation of which depends on the charge of the integration capacitor, at least one MOS transistor operating subthreshold, and the drain-source current of which influences the charge on the integration capacitor, and at least one photodiode operating in photovoltaic mode and connected to the gate of this transistor, such that the drain-source current of the MOS transistor depends on the optical power received by the photodiode.

17 Claims, 5 Drawing Sheets

(51) Int. Cl.

| | | |
|---|---|---|
| *G01J 1/46* | (2006.01) | |
| *G06N 3/04* | (2006.01) | |
| *H04N 5/3745* | (2011.01) | |
| *H04N 5/378* | (2011.01) | |
| *G01J 1/44* | (2006.01) | |

(52) U.S. Cl.
CPC ............... *G01J 1/46* (2013.01); *G06N 3/04* (2013.01); *H04N 5/378* (2013.01); *H04N 5/37452* (2013.01); *G01J 2001/446* (2013.01)

(58) Field of Classification Search
CPC ..... G01J 2001/446; G06N 3/04; G06N 3/063; G06N 3/049; H04N 5/37452; H04N 5/378; A61F 9/00; H01L 27/14643
See application file for complete search history.

(56) References Cited

U.S. PATENT DOCUMENTS

| | | | |
|---|---|---|---|
| 6,046,444 A | 5/2000 | Miyamoto et al. | |
| 2002/0111655 A1 | 8/2002 | Scribner | |
| 2004/0036009 A1* | 2/2004 | Takayanagi | H04N 5/361 250/208.1 |
| 2005/0280713 A1* | 12/2005 | Hagihara | H04N 5/235 348/E3.018 |
| 2006/0214907 A1* | 9/2006 | Devos | G02B 26/0833 345/108 |
| 2008/0284890 A1* | 11/2008 | Miyatake | H04N 3/155 348/308 |
| 2015/0362756 A1* | 12/2015 | Wiser | G02C 7/049 351/210 |

OTHER PUBLICATIONS

International Search Report with English Translation for PCT/EP2018/079119 dated Jan. 25, 2019 (7 pages).
Written Opinion of the International Searching Authority with English Translation for PCT/EP2018/079119 dated Jan. 25, 2019 (13 pages).

* cited by examiner

OPTICAL SENSOR

TECHNICAL FIELD AND BACKGROUND

The present invention relates to a low-power circuit able to reproduce certain behaviours of a biological retina, and especially usable in bio-inspired architectures.

Various systems for acquiring and processing visual information, and implants for treating visual impairments have already been provided.

Patent application FR 2 953 394 discloses an artificial retina including a substrate, a first layer placed thereon comprising portions made of photovoltaic material that are separated by a portion made of insulating material and a second layer placed on the first and comprising portions made of conductive material that are separated by a portion made of insulating material.

The system described in U.S. Pat. No. 5,865,839 is sufficiently small to be able to be implanted in the human eye, and comprises a set of artificial retinas each of which includes a detector element and an optical fibre for directing the incident light toward the detector element. The latter emits an output signal that depends on the intensity of the incident light. A coupler allows this output signal to be coupled to the human retina.

U.S. Pat. No. 5,024,223 discloses an implant including a matrix array of photodiodes that is implanted between the internal and external layers of a human retina. The photoactive area of each photodiode points towards the incident light. The implant produces an amplitude-modulated current in order to electrically stimulate the internal layer of the retina.

U.S. Pat. No. 6,046,444 discloses a pixel structure including a photodiode operating in photoamperic mode in which it is reverse biased, its anode being connected to ground and its cathode to the gate of an NMOS transistor configured in source-follower mode.

SUMMARY

The invention aims to further improve optical sensors and retinal implants in particular, especially in order to provide a high-performance sensor with an extremely low electrical power consumption and that is capable of simulating, to a certain extent, the behaviour of the retina.

The invention thus relates, according to a first of its aspects, to an optical sensor, especially an artificial retina, comprising at least one photosensitive cell, each cell including:
  an integration capacitor,
  a read circuit the operation of which depends on the charge on the integration capacitor,
  at least one MOS transistor operating subthreshold, and the drain-source current of which influences the charge on the integration capacitor,
  at least one photodiode operating in photovoltaic mode and connected to the gate of this transistor, such that the drain-source current of the MOS transistor depends on the optical power received by the photodiode.

When a transistor is operated subthreshold its drain-source current varies exponentially with the gate control voltage in the region called the weak-inversion region (or "subthreshold region") of the transistor, in which region the gate-source voltage is below the threshold voltage at which the inversion zone appears, i.e. at which a conduction channel is created between the drain and the source.

The open-circuit voltage of the photodiode, $V_{co}$, resulting from photoelectric conversion, is applied to the gate of the transistor. As the relationship between the photo-current and the photovoltaic voltage $V_{co}$ of the photodiode is logarithmic, the drain current is substantially proportional to the photoelectric current, and therefore to optical power. This is a noteworthy result and allows the cell to have a substantially linear response to illumination.

The invention also makes large-scale integration of the optical sensor possible, because of the possibility of using a standard industrial CMOS technology.

The MOS transistor may be arranged within the cell, either to charge the integration capacitor, or to discharge it, depending on how the read circuit behaves with the level of charge on this capacitor, and depending on the way in which it is desired for the cell to behave under the received illumination.

Thus, the aforementioned MOS transistor may be an activation transistor arranged to charge the integration capacitor when the photodiode connected to its gate is illuminated. In this case, the activation transistor is preferably of PMOS type.

As a variant, the MOS transistor may be a deactivation transistor arranged to discharge the integration capacitor when the photodiode connected to its gate is illuminated. In this case, the deactivation transistor is preferably of NMOS type.

The cell may include a plurality of activation transistors mounted in parallel and each controlled by one photodiode connected to a respective gate and operating in photovoltaic mode, each activation transistor being arranged to charge the integration capacitor when the photodiode is illuminated, the currents being added algebraically at the same node.

The cell may also include a plurality of deactivation transistors mounted in parallel and each controlled by one photodiode connected to a respective gate and operating in photovoltaic mode, each deactivation transistor being arranged to discharge the integration capacitor when the photodiode is illuminated, the currents being added algebraically at the same node.

It is thus possible to produce a cell comprising as many photodiodes as desired and to produce, depending on the number of activation and deactivation transistors used and the spatial arrangement of the corresponding photodiodes, as many cells having as many different behaviours under light.

Thus, in the examples of implementation of the invention, the cell includes:
  at least one MOS activation transistor, operating subthreshold, and the drain-source current of which influences the charge on the integration capacitor,
  at least one photodiode operating in photovoltaic mode and connected to the gate of this activation transistor, such that the drain-source current depends on the optical power received by the photodiode, the activation transistor being arranged to charge the integration capacitor when the photodiode is illuminated,
  at least one MOS deactivation transistor, operating subthreshold, and the drain-source current of which influences the charge on the integration capacitor,
  at least one photodiode operating in photovoltaic mode and connected to the gate of this deactivation transistor, such that the drain-source current depends on the optical power received by the photodiode, the deactivation transistor being arranged to discharge the integration capacitor when the photodiode is illuminated.

In biology, the neurons of the various layers of the retina each cover one region of our visual field. This spatial region in which the presence of a suitable stimulus modifies the nervous activity of a neuron is called the receptive field of this neuron. Thus, the receptive fields of bipolar and ganglion cells are of circular shape. Their centre and periphery however operate in opposition: a light ray that strikes the centre of the field will have the opposite effect when it falls on the periphery. There are two types of bipolar cell that differ in the way in which their receptive fields respond. If a light stimulus on the centre has the effect of exciting the bipolar cell, the latter undergoes a depolarization. The cell is then said to be of "ON" type. A light ray that only falls on the periphery of the field of this cell will have the opposite effect, i.e. a hyperpolarization of the membrane. Other bipolar cells, of "OFF" type, will show exactly the opposite behaviour: light on the centre produces a hyperpolarization whereas a light stimulus on the periphery has the effect of exciting the cell.

The advantage of ON and OFF cells is that a contrast between the centre and periphery of a zone is detected rather than an optical-power value at a point.

By analogy with the biological retina, the cell may be of "ON" type, including a plurality of deactivation transistors and associated photodiodes, the photodiode associated with the activation transistor being surrounded by the photodiodes associated with the deactivation transistors.

The cell may be of "OFF" type, including a plurality of activation transistors and associated photodiodes, the photodiode associated with the deactivation transistor being surrounded by the photodiodes associated with the activation transistors. The photodiodes associated with the deactivation transistors in the case of an "ON" cell or the photodiodes associated with the activation transistors in the case of an "OFF" cell, may be arranged in a polygonal grid, especially with at least four photodiodes and corresponding transistors of the deactivating type, activating type, respectively, within the cell.

The sensor may be supplied with electrical power in various ways.

The optical sensor preferably includes a stand-alone electrical power source that is preferably photovoltaic. It may thus include one or more photodiodes of the same type as the one or more photosensitive cells, dedicated to supplying power to the sensor, and preferably a plurality of photodiodes mounted in series, so as to increase the delivered voltage.

The electrical power supplying photodiodes may have various arrangements.

Preferably, the stand-alone electrical power source includes a plurality of photodiodes placed around a matrix of photosensitive cells or distributed between the photosensitive cells.

The read circuit may be produced in various ways. It must be sensitive to a low synaptic current, this being the reason why one or more transistors operating subthreshold are used in the cell.

The read circuit may itself consist of any type of common measuring circuit, there being no specific constraints with respect to current or voltage operation.

Preferably, the read circuit includes at least one artificial neuron.

For example, the artificial neuron may be a spiking neuron of Axon-Hillock type, Morris-Lecar type, etc.

By analogy with biology, the photodiode may then correspond to a cone or a rod, the associated transistor to one or more amacrine, bipolar and horizontal cells and the artificial neuron to a spike-generating ganglion cell.

Advantageously, the artificial neuron is arranged to generate spikes at a frequency that depends on the level of charge on the integration capacitor, and therefore on the optical power received by at least one photodiode.

Preferably, the artificial neuron has a very low electrical power consumption, and uses transistors operating subthreshold, so as to function with a low supply voltage ($V_{dd} < V_t$).

In a way that is altogether preferred, at least the spiking circuit of the artificial neuron is supplied with power by a power supply ($V_N$, $V_P$) the negative voltage ($V_N$) of which is comprised between −200 mV and 0 mV and the positive voltage ($V_P$) of which is comprised between 0 mV and +200 mV.

Preferably ($V_P - V_N$) < $V_{th}$, $V_{th}$ being the threshold voltage of all the MOS transistors of the artificial neuron. For simplicity's sake, to make the respective voltages supplying the neuron and sensor the same, $V_p$ is preferably chosen to be equal to $V_{dd}$.

According to one altogether privileged variant, the artificial neuron includes:
  an external synaptic current input defined by a terminal of the integration capacitor and which performs the algebraic sum of the activation and deactivation currents,
  a negative-feedback spiking circuit, including:
    a bridge comprising PMOS and NMOS transistors in series and the drains of which are connected by a midpoint to the integration capacitor, this midpoint defining the output of the artificial neuron,
    at least one so-called delay capacitor between the gate and the source of one of the transistors of the bridge,
    only two CMOS inverters in cascade, each consisting of two transistors, the input of the first inverter being connected to the integration capacitor and its output to the input of the second inverter and to the gate of one of the transistors of the bridge, the output of the second inverter being connected to the gate of the other transistor of the bridge, or
    only three CMOS inverters, two inverters of which are in cascade, each consisting of two transistors, the input of the first inverter being connected to the integration capacitor and its output to the input of the second inverter, the output of the second inverter being connected to the gate of one of the transistors of said bridge, the input of the third CMOS inverter being connected to the integration capacitor and the output of the third CMOS inverter being connected to the gate of the other transistor of said bridge.

All the transistors of the artificial neuron preferably operate subthreshold, thus engendering a low electrical power consumption. The invention also relates, independently of or in combination with the above, to the following variants such as defined below:
  Artificial neuron including:
    an external synaptic current input defined by a terminal of the integration capacitor and which performs the algebraic sum of the activation and deactivation currents,
    a negative-feedback spiking circuit, supplied with power by a power supply the negative voltage of which is comprised between −200 mV and 0 mV and the positive voltage of which is comprised between 0 mV and +200 mV, including:
      a bridge comprising PMOS and NMOS transistors in series and the drains of which are connected by a midpoint to the integration capacitor, this midpoint defining the output of the artificial neuron, at least one so-called delay capacitor between the gate and the source of one of the transistors of the bridge, at least two CMOS inverters between the integration capacitor and the gates of the transistors of said bridge so as to cause the transistors of the bridge to change state depending on the voltage of the integration capacitor and to allow the spiking circuit to generate at least one spike when the voltage of the integration capacitor crosses a predefined threshold, with charge on the integration capacitor via one of the transistors of the bridge and discharge via the other transistor.

Artificial neuron including:

an external synaptic current input defined by a terminal of the integration capacitor and which performs the algebraic sum of the activation and deactivation currents, a negative-feedback spiking circuit, including:
  a bridge comprising PMOS and NMOS transistors in series and the drains of which are connected by a midpoint to the integration capacitor, this midpoint defining the output of the artificial neuron,
  at least one so-called delay capacitor between the gate and the source of one of the transistors of the bridge,
  at least two CMOS inverters between the integration capacitor and the gates of the transistors of said bridge so as to cause the transistors of the bridge to change state depending on the voltage of the integration capacitor and to allow the spiking circuit to generate at least one spike when the voltage of the integration capacitor crosses a predefined threshold, with charge on the integration capacitor via one of the transistors of the bridge and discharge via the other transistor.

said neuron being noteworthy in that the capacitance of the delay capacitor connected to the NMOS transistor is higher than the capacitance of the integration capacitor.

Artificial neuron including:

an external synaptic current input defined by a terminal of the integration capacitor and which performs the algebraic sum of the activation and deactivation currents, a negative-feedback spiking circuit, including:
  a bridge comprising PMOS and NMOS transistors in series and the drains of which are connected by a midpoint to the integration capacitor, this midpoint defining the output of the artificial neuron,
  at least one so-called delay capacitor between the gate and the source of one of the transistors of the bridge,
  at least two CMOS inverters between the integration capacitor and the gates of the transistors of said bridge so as to cause the transistors of the bridge to change state depending on the voltage of the integration capacitor and to allow the spiking circuit to generate at least one spike when the voltage of the integration capacitor crosses a predefined threshold, with charge on the integration capacitor via one of the transistors of the bridge and discharge via the other transistor.

said neuron being noteworthy in that it includes two CMOS inverters in cascade, the input of the first inverter being connected to the integration capacitor and its output to the input of the second inverter, the output of the second inverter being connected to the gate of one of the transistors of said bridge, and a third CMOS inverter the input of which is connected to the integration capacitor and the output to the gate of the other transistor of said bridge.

In other variants, the read circuit comprises a neural network.

Advantageously, this neural network includes at least two artificial neurons called the pre-neuron and post-neuron, which are connected together by a synaptic circuit taking the form of an excitatory or inhibitory synapse.

Excitatory synapses promoting the creation of an action potential by the post-neuron, depolarize the membrane of the post-neuron (i.e. increase its potential) and have a similar role to that of sodium channels in biology.

Inhibitory synapses hindering the creation of an action potential by the post-neuron, hyperpolarize the membrane of the post-neuron (i.e. decrease its potential) and have a similar role to that of potassium channels in biology.

In certain privileged sub-variants, said neural network employs neurons comprising transistors operating sub-threshold. In this case, advantageously, an excitatory synapse may be represented by two series transistors connected between the positive supply $V_P$ and the membrane of the post-neuron:
  a PMOS transistor the gate of which is connected to the inverted membrane voltage of the pre-neuron. This signal may be collected on output from any suitable inverter (belonging to the artificial neuron or not), the source being at the potential $V_P$.
  an (N or P) MOS transistor the gate of which is connected to a control voltage V1 that allows the charging current of the membrane of the post-neuron to be controlled.

Advantageously, an inhibitory synapse may be represented by two series transistors connected between the membrane of the post-neuron and the negative supply $V_N$:
  an NMOS transistor the gate of which is connected to the output of two inverters in cascade the input of which is the membrane voltage of the pre-neuron. This signal may be collected on output from a suitable pair of inverters in cascade (belonging to the artificial neuron or not), the source being at the potential $V_N$.
  an (N or P) MOS transistor the gate of which is connected to a control voltage V1 that allows the discharging current of the membrane of the post-neuron to be controlled.

According to the invention, each photosensitive cell advantageously includes a plurality of photodiodes and associated transistors, forming as many pixels of the sensor, and a single read circuit per cell. The pixels may be of the same size, and have the same photodiode area. However, the pixels may be of different size, as is the case for logarithmic sensors for example.

Lastly, in order to make the sensor more sensitive to low light levels and less sensitive to high light levels and thus to limit the frequency of the spikes to a frequency band that is not very sensitive to the absolute value of the light level, via automatic gain control, it may be useful to stabilize the neuron under high light levels and to destabilize it under low light levels.

This may be done in advanced variants of the sensor using a photodiode (or a set of photodiodes) to command one (or a plurality of) transistor(s) playing the role of inhibitory synapse(s).

At low light levels, this synapse has no effect and the neuron can be made very sensitive. At high light levels, the current generated in the inhibitory synapse inhibits the membrane, decreasing its sensitivity.

BRIEF DESCRIPTION OF THE DRAWINGS

The invention will possibly be better understood on reading the following detailed description of nonlimiting examples of implementation thereof, and on examining the appended drawing, in which.

DETAILED DESCRIPTION

Figure 1:
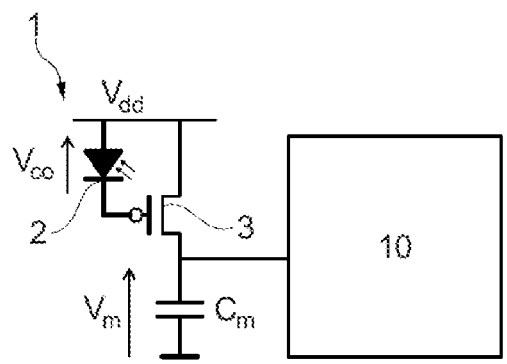
FIGS. 1 and 2 are schematic representations of a sensor according to the invention.
Figure 2:
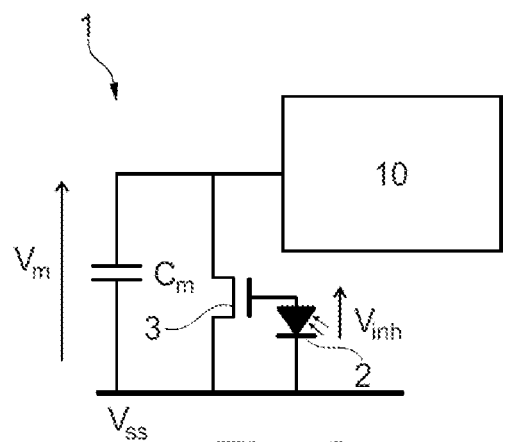

FIGS. 1 and 2 schematically show an optical sensor 1 according to the invention. Such a sensor may include, as illustrated, a PMOS transistor 3, a photodiode 2, an integration capacitor $C_m$ and a read circuit 10.

In FIG. 1, the photodiode 2 is connected to the gate of the transistor 3 by its cathode, its anode being connected to the supply voltage $V_{dd}$. The drain of the transistor 3 is connected to a terminal of the integration capacitor $C_m$ also forming an input-output of the read circuit 10.

The photodiode 2 operates in open-circuit photovoltaic mode in which the voltage across its terminals is strictly positive, $V_{co} > 0$, and the current flowing through it is zero. In this mode, the photodiode is capable of generating power, contrary to the usual mode (receiver mode) in which the photodiode is reverse biased.

The transistor 3 operates subthreshold, and the drain current in the latter varies exponentially with the gate-source voltage, and therefore with the open-circuit voltage of the photodiode 2. The transistor 3 operating subthreshold is comparable to an excitatory synapse.

From the current-voltage relationship of the PMOS transistor, a relationship between the open-circuit voltage $V_{co}$ generated by the photodiode and the current $I_{ds}$ output by the transistor is obtained:

$$I_{ds} = G_p \cdot \exp\left(-\frac{V_{gs}}{\eta \cdot V_t}\right) \cdot (V_{dd} - V_m) = G_p \cdot \exp\left(\frac{V_{CO}}{\eta \cdot V_t}\right) \cdot (V_{dd} - V_m) \quad (1)$$

In equation (1), $G_p$ is the conductance of the transistor, $\eta$ is the ideality factor of the current-voltage characteristic $I_{ds}(V_{gs})$ of the transistor and $V_m$ is the voltage across the terminals of the capacitor such as shown.

The cathode of the photodiode is connected to the gate of the PMOS transistor. This de facto means that the total current I of the photodiode, which is given by the following expression, will be zero:

$$I = I_s\left(\exp\left(\frac{V}{nV_t}\right) - 1\right) - I_{ph} \quad (2)$$

where $V_t = kT/q$ is the thermal voltage, $I_s$ is the saturation current of the PN junction forming the photodiode and $I_{ph}$ the photocurrent generated by the photodiode, which current is defined by:

$$I_{ph} = \frac{qQP_{opt}}{hv} \quad (3)$$

where q is the charge on an electron, h Planck's constant, v the frequency of the optical signal, Q the quantum efficiency and $P_{opt}$ optical power.

As a result, the illumination produces an open-circuit photovoltaic voltage $V_{co}$ that may be expressed thus:

$$V_{co} = nV_t \cdot \text{Ln}\left(1 + \frac{I_{ph}}{I_s}\right) \quad (4)$$

where n is the ideality factor of the voltage-current characteristic of the photodiode.

Inserting (4) into (1), the following is obtained:

$$I_{ds} = G_p \cdot \left(1 + \frac{I_{ph}}{I_S}\right)^{\frac{n}{\eta}} \cdot (V_{dd} - V_m) \quad (5)$$

Assuming that the ideality factors n and $\eta$ are of the same order of magnitude, the expression of the drain-source current of the transistor 3 that influences the charge on the integration capacitor $C_m$ is obtained:

$$I_{ds} = G_p \cdot \left(1 + \frac{I_{ph}}{I_S}\right)(V_{dd} - V_m) \quad (6)$$

In the most frequent case, the photo-current $I_{ph}$ is much larger than the reverse current $I_s$ of the unbiased junction. Thus:

$$I_{ds} = \frac{G_p}{I_s} \cdot I_{ph} \cdot (V_{dd} - V_m) \quad (7)$$

A substantially linear relationship between the drain-source current and the photocurrent, and therefore between the drain-source current and the received optical power, is thus obtained.

In FIG. 2, the photodiode 2 is connected to the gate of the transistor 3 by its anode, its cathode being connected to the supply voltage $V_{ss}$. The drain of the transistor 3 is connected to a terminal of the integration capacitor $C_m$ also forming an input-output of the read circuit 10. The transistor 3 operating subthreshold is comparable to an inhibitory synapse.

Figure 3:
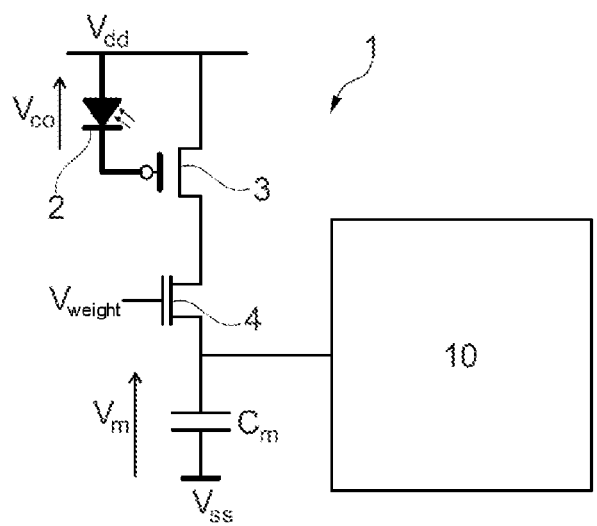
FIG. 3 illustrates an example of adjustment of synaptic weight in the case of a photodiode associated with a transistor operating subthreshold by way of excitatory synapse.

If the read circuit 10 is an artificial neuron, this drain-source current may be called a synaptic current. The 'weight' of the synapse may be adjusted for example:

- by suitably choosing the dimensions of the transistor, and in particular the conductance $G_p$ of the transistor, which is proportional to the width of the gate and inversely proportional to its length,
- using an (N or P) adjustment transistor 4 placed between the transistor 3 that operates subthreshold and the integration capacitor $C_m$ (when the transistor 3 may be likened to an excitatory synapse, said adjustment transistor 4 is placed between the drain of the transistor 3 operating subthreshold and the integration capacitor $C_m$, as shown in FIG. 3).

The overall synaptic current may excite or inhibit the artificial neuron, inter alia depending on the role of the transistor 3 operating subthreshold (excitatory or inhibitory synapse, respectively).

The neuron may be easily connected to the neighbouring photovoltaic cells in order to create cells that are sensitive to contrast, as in a biological retina.

Figure 4:
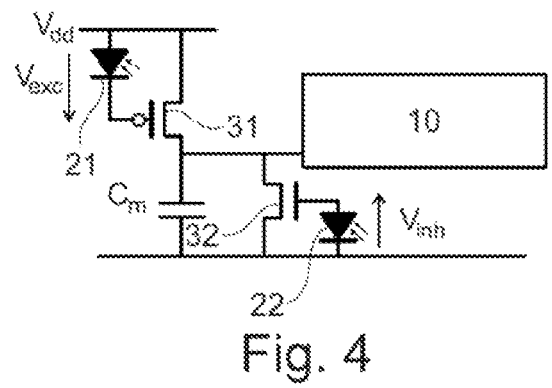
FIG. 4 shows an elementary association of an activating transistor and a deactivating transistor within a sensor according to the invention.

FIG. 4 illustrates an example of elementary connection of photodiodes in an excitation or inhibition configuration.

Without applied optical power, the neuron 10 may be stable (does not generate spikes) or unstable (generation of spikes at low frequency).

The photodiode 21 is connected to a PMOS transistor 31 that is equivalent to an excitatory synapse of the artificial neuron 10. It tends to promote the generation of spikes by the neuron 10 or to increase the frequency of said spikes. The photodiode is connected to an NMOS transistor 32 that is equivalent to an inhibitory synapse. It tends to decrease the aforementioned frequency. Since the photodiodes operate in open circuit, the same photodiode may be connected to various synapses without modification of the properties thereof.

As a variant, more complex processing of the received optical signals may be performed by associating a plurality of photodiodes with the same neuron 10.

Any combination of activation and deactivation transistors is possible, because all the currents will be added algebraically at the same node i.e. the node forming the input-output of the neuron.

It is thus possible to for example create equivalents of the ON and OFF cells of the biological retina.

Figure 5:
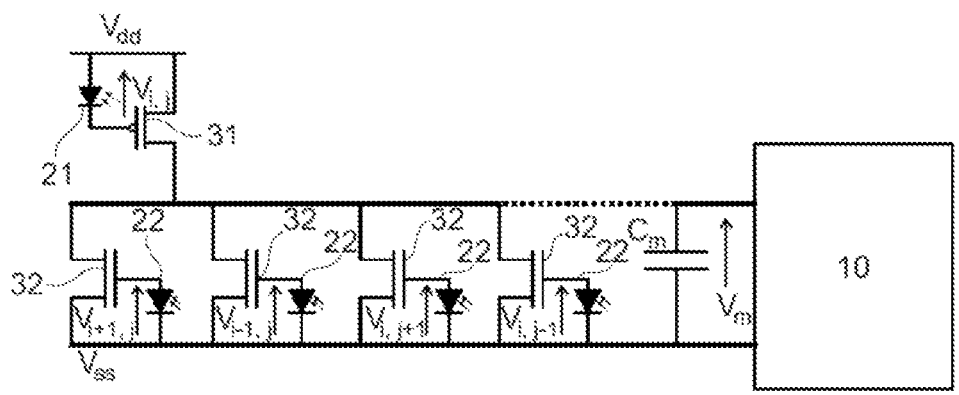
FIGS. 5 and 6 illustrate the implementation of an ON cell and of an OFF cell, respectively.

FIG. 5 shows an artificial implementation of an ON cell with a photodiode 21 associated with an activating transistor 31 playing the role of excitatory synapse at the centre and a plurality of photodiodes 22 associated with deactivating transistors 32 arranged in parallel and playing the role of inhibitory synapses on the perimeter. The number of photodiodes 22 associated with the deactivating transistors 32 will be chosen depending on the application and on the targeted characteristics.

Figure 6:
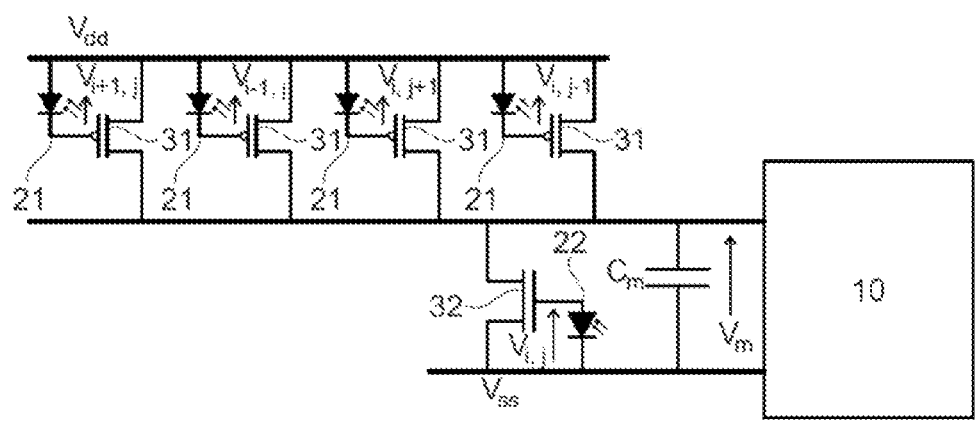

FIG. 6 shows an artificial implementation of an OFF cell with a photodiode 22 associated with a deactivating transistor 32 playing the role of inhibitory synapse at the centre and a plurality of photodiodes 21 associated with activating transistors arranged in parallel and playing the role of excitatory synapses on the perimeter.

Figure 7:
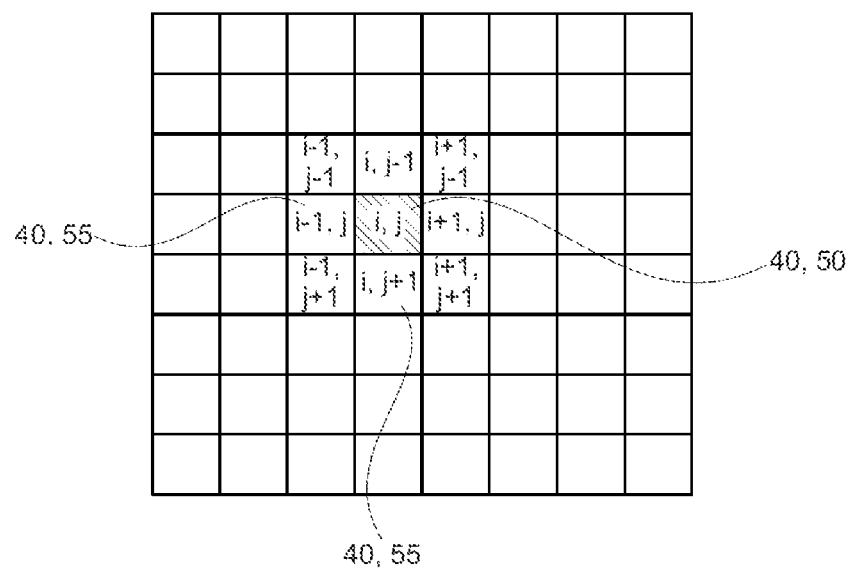
FIGS. 7 and 8 are matrix representations of an ON or OFF cell showing a central pixel and its neighbours, in a rectangular grid and hexagonal grid arrangement, respectively.

FIG. 7 describes an elementary association, a "square" (square or rectangular) type matrix of 40 pixels being considered, among which pixels subsets formed of central pixels 50 and peripheral pixels 55 may be considered. If parallels are drawn to FIG. 5 (schematic showing an ON cell), the pixel 50 at the centre of FIG. 7 corresponds to the photodiode the cathode of which is connected to the gate of the activating PMOS transistor (excitatory synapse), whereas the four peripheral pixels 55 encircling the pixel of the centre 50 have their cathode connected to ground and their anode connected to the gate of a deactivating NMOS transistor (inhibitory synapse).

For a uniform illumination of the photodiodes, the artificial neuron will have a relatively low, or even zero spike frequency.

If the pixel 50 at the centre is strongly illuminated, the overall excitation current delivered to the membrane of the neuron will increase and the pulse frequency also.

If the peripheral pixels 55 of the perimeter are strongly illuminated, the sum of the inhibition currents will be higher than the excitation current and the neuron will no longer generate spikes (or very few; i.e. the spike frequency is relatively low, or even zero as in the case of uniform illumination).

An architecture that is the twin of that of the circuit of FIG. 7 may also be used in order to obtain an OFF cell such as shown in FIG. 6 in which the pixel 50 of the centre is associated with an inhibitory synapse (photodiode connected to a deactivating transistor) and the four peripheral pixels 55 of the perimeter are associated with excitatory synapses (photodiodes connected to activating transistors).

Figure 8:
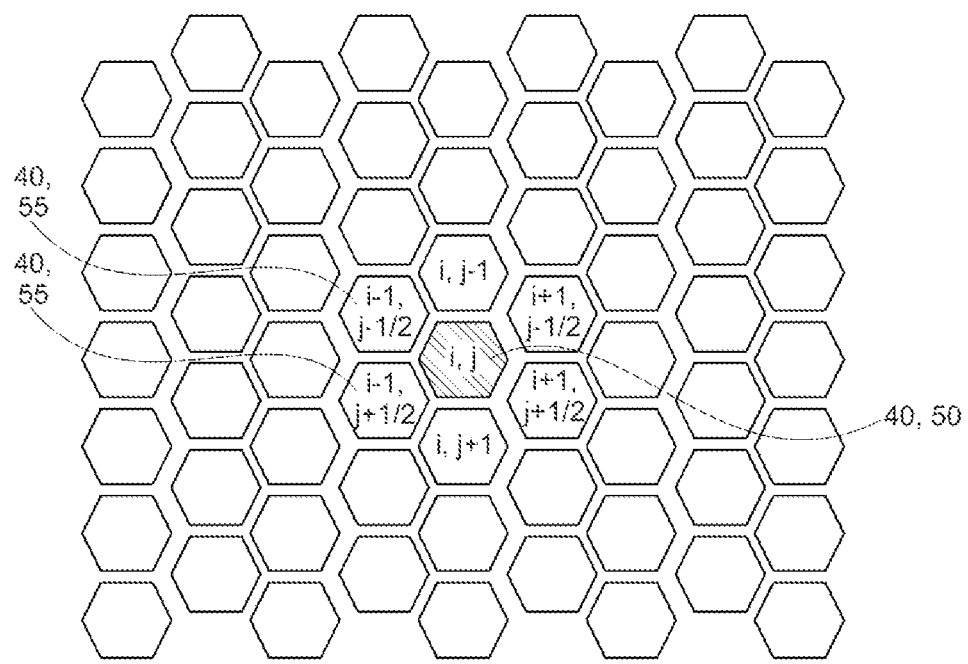

The topology organized into a "square" type matrix may be changed into a hexagonal configuration such as that shown in FIG. 8. Any polygonal topology is of course possible.

Generally, for an association of N exciting pixels and M inhibiting pixels, the total synaptic current $I_{tot}$ applied to the neuron is expressed thus:

$$I_{tot} = (V_{dd} - V_m) \sum_{i=1}^{N} G_{exc,i} \cdot \left(1 + \frac{I_{exc,i}^{ph}}{I_{s,i}}\right) - (V_m) \sum_{j=1}^{M} G_{inh,j} \cdot \left(1 + \frac{I_{inh,j}^{ph}}{I_{s,j}}\right). \quad (8)$$

In a normal operation of the photodiode, the photo-current $I_{ph}$ is much larger than the reverse current $I_s$ of the various junctions. Then:

$$I_{tot} = (V_{dd} - V_m) \sum_{i=1}^{N} \frac{G_{exc,i}}{I_{s,i}} \cdot I_{exc,i}^{ph} - (V_m) \sum_{j=1}^{M} \frac{G_{inh,j}}{I_{s,j}} \cdot I_{inh,j}^{ph}. \quad (9)$$

Depending on the application, the conductances $G_{exc,i}$ and $G_{inh,i}$ of the transistors will possibly be adjusted by adjusting parameters of the transistors (gate width and length for example).

Figure 9:
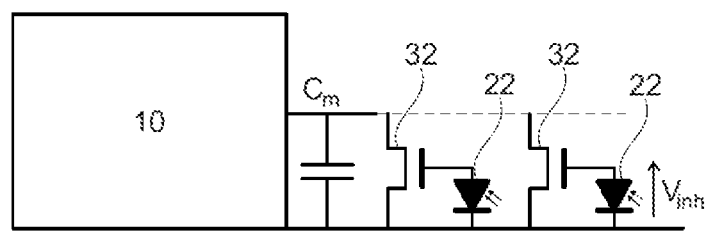
FIG. 9 illustrates an example of control of the frequency of the spikes depending on the optical power received by a certain number of pixels.

As the human eye does very well, it is desirable for an artificial vision system to be able to adapt to the average luminance of a scene and to be able to detect outlines and shapes both at low and high luminosities. To do this, it is possible to use, as illustrated in FIG. 9, a plurality of deactivating transistors 32. Thus, for high luminosities, the neuron will be hyperpolarized by a high current in the deactivating transistors 32, thereby creating a leakage that discharges the integration capacitor, and in case of low luminosity, the neuron will be depolarized by the decrease or disappearance of this leakage current.

Figure 10:
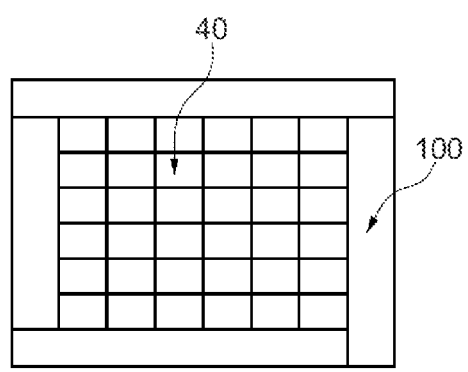
FIGS. 10 and 11 show the arrangement of a photovoltaic power supply external to or integrated into the sensor, respectively.
Figure 11:
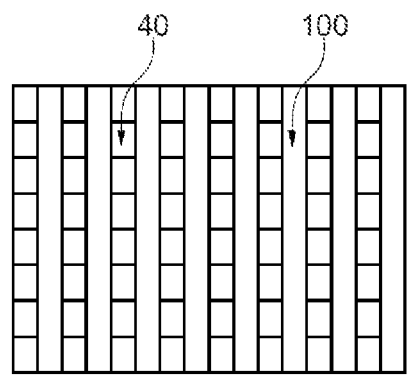
Figure 12:
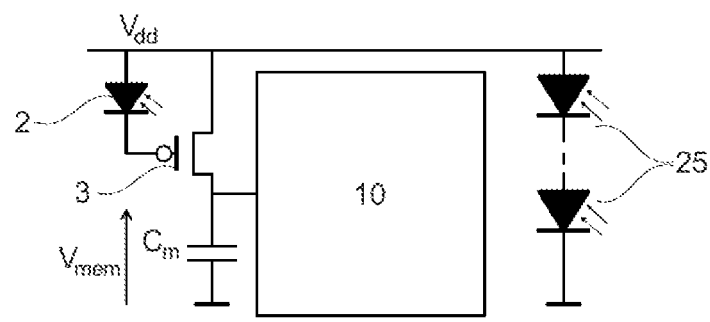
FIG. 12 illustrates an example of an integrated photovoltaic power supply.

FIGS. 10 and 11 show two ways of producing the power required for the operation of an optical sensor 1. In FIG. 10, photovoltaic supply cells 100 are placed around the pixels, and in FIG. 11, these cells are arranged in rows alternating with those of the pixels. In the case where the power supply is integrated into the sensors, to generate a sufficient voltage, of a few hundred mV, two or more diodes 25 will possibly be placed in series, as illustrated in FIG. 12.

Figure 13:
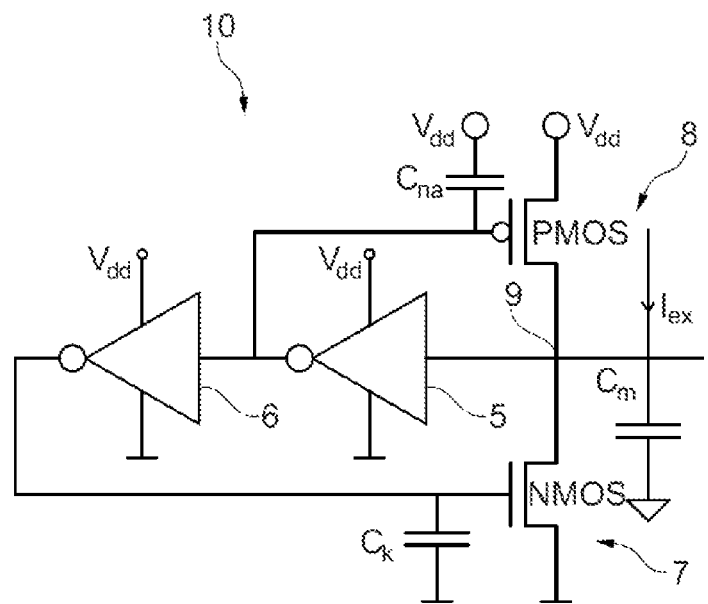
FIGS. 13 and 14 show structural examples of an artificial neuron comprising two inverters and three inverters, respectively.

FIG. 13 schematically illustrates an example embodiment of the artificial neuron 10. In this example, the artificial neuron 10 includes two inverters 5 and 6 that are connected in cascade, the output of the first being connected to the input of the second. The output of the first inverter 5 is connected to the gate of a PMOS transistor 8. The output of the second inverter is connected to the gate of an NMOS transistor 7.

The transistors 7 and 8 are electrically connected in series and form a bridge between the supply voltage $V_{dd}$ and ground. The midpoint 9, which is defined by the connection of the drains of the transistors of the bridge, is connected to a terminal of the integration capacitor $C_m$. The other terminal of the integration capacitor $C_m$ is connected to ground.

A capacitor $C_k$ is connected between ground and the gate of the NMOS transistor 7. A capacitor $C_{na}$ is connected between $V_{dd}$ and the gate of the PMOS transistor 8.

$I_{ex}$ is the external excitation current, which charges or discharges the integration capacitor $C_m$ and which originates from the one or more activation or deactivation transistors.

When the potential across the terminals of the integration capacitor $C_m$ reaches the threshold voltage of the first inverter 5, a corresponding potential is then transmitted, after a first inversion by the inverter 5, to the gate of the PMOS transistor, activating the latter after a delay defined by the capacitor $C_{na}$. Thus, the integration capacitor $C_m$ is charged by the open conduction channel of the PMOS transistor 8. This charge corresponds to the rising front of the output action potential.

When the threshold voltage of the second inverter 6 is reached, a corresponding potential is transmitted to the gate of the NMOS transistor 7, activating the latter after a delay defined by the delay capacitor $C_k$, which is in the considered example longer than the activation delay of the PMOS, because of the choice of $C_k > C_{na}$. Thus, after having had the time to charge, the integration capacitor $C_m$ starts to discharge on the opening of the conduction channel of the NMOS transistor 7. This discharge corresponds to the falling front of the output action potential.

Figure 14:
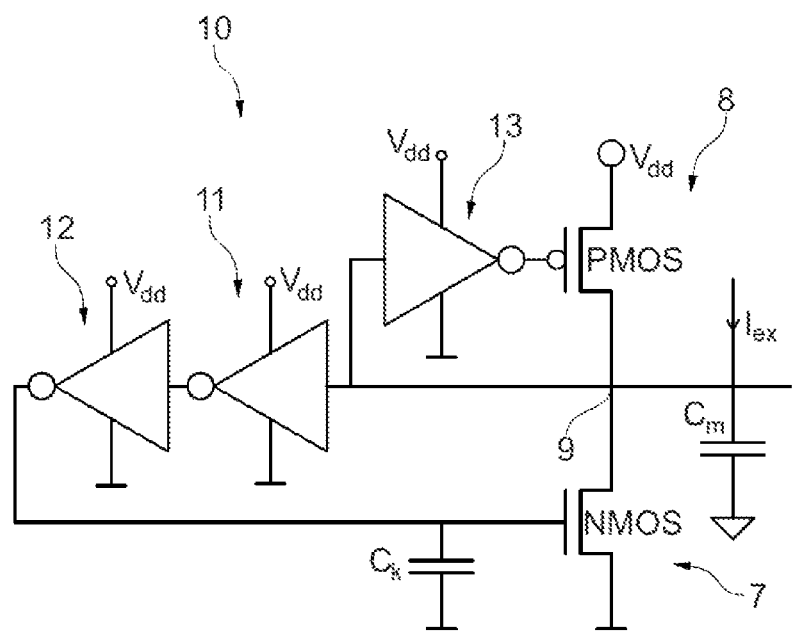

FIG. 14 schematically shows an artificial neuron 10 according to another example embodiment, which differs from that of FIG. 13 in that a third inverter 12 has been added, the first inverter 13 transmitting the output potential after inversion to the gate of the PMOS transistor 8 of the bridge and the two other inverters 11 and 12, which are connected in cascade, transmitting the output potential to the gate of the NMOS transistor 7.

The inputs of the inverters 13 and 11 are connected to the midpoint 9 of the bridge and to the integration capacitor, and the input of the inverter 12 is connected to the output of the inverter 11.

The addition of the third inverter allows the commands of the transistors of the bridge to be optimized independently, by independently adjusting the threshold voltages of the inverters.

The adjustment of the voltage gain and of the threshold voltages of the inverters influences the operation of the artificial neuron 10.

Preferably, the threshold voltage of the neurone that produces the action potential is the threshold voltage of the inverter supplying the PMOS transistor of the bridge with power. The number of inverters used may be defined depending on speed or power-consumption objectives.

Among the variants in which the read circuit comprises not a single neuron comprising transistors operating subthreshold but rather a network of neurons comprising transistors operating subthreshold, the subvariants in which the synaptic circuit possesses two inputs and includes two transistors that are connected in series by their drains will be preferred, at least one of said transistors being of NMOS type and being controlled by a gate potential corresponding to the first input of the synaptic circuit, the gate of the second transistor corresponding to the second input of the synaptic circuit, and the output of the synaptic circuit, corresponding to the source of the NMOS transistor, being connected to the output potential of the post-neuron.

By way of example, said synaptic circuit may correspond to:
- an excitatory synapse wherein the second input of the synaptic circuit is connected to the output of an inverter (preferably the first inverter of the pre-neuron) having for input the membrane potential of the pre-neuron, and in particular to the gate of the PMOS transistor of the bridge of the pre-neuron, or
- an inhibitory synapse wherein the second input of the synaptic circuit is connected to the output of two inverters in series (preferably the two inverters in cascade of the pre-neuron) the input of the first of which is subjected to the membrane potential of the pre-neuron, or
- an inhibitory synapse wherein the second input of the synaptic circuit is connected to the gate of the NMOS transistor of the bridge of the pre-neuron.

Of course, the invention is not limited to the example embodiments that have just been described.

The invention is most particularly applicable to retinal implants, but nevertheless covers a broad spectrum of applications. It may for example be used in robotics, home automation, the processing of images and videos, etc. The architecture of the artificial neuron associated with a cell of the optical sensor according to the invention may be different from the architectures described above.

The invention claimed is:

1. An optical sensor comprising at least one photosensitive cell, each cell including:
    an integration capacitor,
    a read circuit the operation of which depends on the charge on the integration capacitor,
    at least one MOS transistor operating subthreshold, and the drain-source current of which influences the charge on the integration capacitor,
    at least one photodiode operating in photovoltaic mode, wherein the photodiode is (a) forward biased or operating with a positive voltage across its anode-cathode (PN) junction and (b) connected to the gate of this transistor, such that the drain-source current of the MOS transistor depends on the optical power received by the photodiode.

2. The optical sensor according to claim 1, the transistor being an activation transistor arranged to charge the integration capacitor when the photodiode connected to its gate is illuminated.

3. The optical sensor according to claim 2, the activation transistor being of PMOS type.

4. The optical sensor according to claim 1, the transistor being a deactivation transistor arranged to discharge the integration capacitor when the photodiode connected to its gate is illuminated.

5. The optical sensor according to claim 4, the deactivation transistor being of NMOS type.

6. The optical sensor according to claim 1, the cell including a plurality of activation transistors mounted in parallel and each controlled by one photodiode connected to a respective gate and operating in photovoltaic mode, each activation transistor being arranged to charge the integration capacitor when the photodiode is illuminated.

7. The optical sensor according to claim 1, the cell including a plurality of deactivation transistors mounted in parallel and each controlled by one photodiode connected to a respective gate and operating in photovoltaic mode, each deactivation transistor being arranged to discharge the integration capacitor when the photodiode is illuminated.

8. The optical sensor according to claim 1, the cell including:
  at least one MOS activation transistor, operating sub-threshold, and the drain-source current of which influences the charge on the integration capacitor,
  at least one photodiode operating in photovoltaic mode and connected to the gate of this activation transistor, such that the drain-source current depends on the optical power received by the photodiode, the activation transistor being arranged to charge the integration capacitor when the photodiode is illuminated,
  at least one MOS deactivation transistor, operating sub-threshold, and the drain-source current of which influences the charge on the integration capacitor, and
  at least one photodiode operating in photovoltaic mode and connected to the gate of this deactivation transistor, such that the drain-source current depends on the optical power received by the photodiode, the deactivation transistor being arranged to discharge the integration capacitor when the photodiode is illuminated.

9. The optical sensor according to claim 8, the cell being of "ON" type, including a plurality of deactivation transistors and associated photodiodes, the photodiode associated with the activation transistor being surrounded by the photodiodes associated with the deactivation transistors.

10. The optical sensor according to claim 8, the cell being of "OFF" type, including a plurality of activation transistors and associated photodiodes, the photodiode associated with the deactivation transistor being surrounded by the photodiodes associated with the activation transistors.

11. The optical sensor according to claim 9, the photodiodes associated with the deactivation transistors in the case of an "ON" cell or the photodiodes associated with the activation transistors in the case of an "OFF" cell, being arranged in a polygonal grid.

12. The optical sensor according to claim 1, including a stand-alone electrical power source.

13. The optical sensor according to claim 12, the stand-alone electrical power source including a plurality of photodiodes placed around a matrix of photosensitive cells or distributed between the photosensitive cells.

14. The optical sensor according to claim 1, the read circuit including at least one artificial neuron.

15. The optical sensor according to claim 14, the artificial neuron generating spikes at a frequency that depends on the optical power received by at least one photodiode.

16. The optical sensor according to claim 14, the artificial neuron including:
  an external synaptic current input defined by a terminal of the integration capacitor and which performs the algebraic sum of the activation and deactivation currents,
  a negative-feedback spiking circuit, including:
    a bridge comprising PMOS and NMOS transistors in series and the drains of which are connected by a midpoint to the integration capacitor, this midpoint defining the output of the artificial neuron,
    at least one so-called delay capacitor between the gate and the source of one of the transistors of the bridge,
  only two CMOS inverters in cascade, each consisting of two transistors, the input of the first inverter being connected to the integration capacitor and its output to the input of the second inverter and to the gate of one of the transistors of the bridge, the output of the second inverter being connected to the gate of the other transistor of the bridge, or
  only three CMOS inverters, two inverters of which are in cascade, each consisting of two transistors, the input of the first inverter being connected to the integration capacitor and its output to the input of the second inverter, the output of the second inverter being connected to the gate of one of the transistors of said bridge, the input of the third CMOS inverter being connected to the integration capacitor and the output of the third CMOS inverter being connected to the gate of the other transistor of said bridge.

17. The optical sensor according to claim 1, each photosensitive cell including a plurality of photodiodes and associated transistors, forming as many pixels of the sensor, and a single read circuit per cell.

* * * * *